United States Patent [19]
Wylie

[11] 4,381,419
[45] Apr. 26, 1983

[54] ADSORPTION-DESORPTION SEPARATION PROCESS WITH INTEGRATED LIGHT AND HEAVY DESORBENTS

[75] Inventor: Roger Wylie, Baytown, Tex.

[73] Assignee: Exxon Research & Engineering Co., Florham Park, N.J.

[21] Appl. No.: 256,651

[22] Filed: Apr. 22, 1981

[51] Int. Cl.³ .............................................. C07C 7/12
[52] U.S. Cl. .................................... 585/828; 203/99; 203/DIG. 19; 585/826
[58] Field of Search ............... 585/826, 828, 820, 825, 585/829, 830; 203/DIG. 19, 99

[56]  References Cited
U.S. PATENT DOCUMENTS
4,246,073  1/1981  Umeda et al. ............. 203/DIG. 19

FOREIGN PATENT DOCUMENTS
2856051  5/1979  Fed. Rep. of Germany ... 203/DIG. 19

Primary Examiner—Delbert E. Gantz
Assistant Examiner—A. Pal
Attorney, Agent, or Firm—Mitchell D. Bittman

[57]  ABSTRACT

An improved adsorption-desorption separation process is disclosed for separating close boiling fractions or isomers of a hydrocarbon feedstream containing mixed hydrocarbon fractions or isomers.

5 Claims, 3 Drawing Figures

ADSORPTION-DESORPTION SEPARATION PROCESS WITH INTEGRATED LIGHT AND HEAVY DESORBENTS

It is well known in the separation art that adsorption can be used to separate close boiling hydrocarbon fractions which would normally be very difficult to separate by fractionation.

It is conventional, for example, to separate $C_8$ isomers, in relatively pure form, by employing a crystalline aluminosilicate adsorbent to selectively adsorb one $C_8$ aromatic isomer from a feed material containing mixed $C_8$ isomers. One such method, for example, which shows this selective adsorption-separation process used for the separation of $C_8$ aromatic isomers, is discussed in U.S. Pat. No. 3,558,732. The desired fraction is adsorbed into the adsorbent and a now desired fraction-free raffinate stream is removed from the adsorption zone.

Once the adsorption of the desired fraction which may be an impurity or desired product has occurred, the solid adsorbent in the adsorption zone is contacted with a desorbent. The specific desorbent is so selected that it will cause competitive desorption between it and the selectively adsorbed component of the feed, thereby affecting the selectivity of the adsorbent for the desired separation. This contact will release the desired fraction from the adsorbent as a relatively concentrated extract stream, and thereby allowing the adsorbent to be regenerated for use as a continuous adsorption-desorption separation process. In addition, as will be more closely shown hereinafter, it is possible to continually recycle the desorbent stream within the process.

The desorbent selection is based upon its compatibility with the desired fraction, and its boiling range in comparison with both the extract and raffinate stream. If the desorbent boils at a lower temperature than the extract stream and raffinate stream, the process is referred to as light; alternatively, if the desorbent boils at a higher temperature than these streams, the process is referred to as heavy.

With specific reference to the adsorption-separation of $C_8$ isomers, as for example, meta, ortho and para-xylene, a light process desorbent may be a $C_7$ compound such as toluene, while a heavy process desorbent may be $C_{10}$ compounds such as para-diethylbenzene or durene.

In a system using the light process there exists a fractionating column for the raffinate fraction and a fractionating column for the extract (product) fraction. A parallel situation exists in the heavy process, namely, a fractionating column for the raffinate fraction and a fractionating column for the extract (product) fraction. Furthermore, in both the light and the heavy process the same desorbent is present in both the raffinate and extract fractions.

The light and heavy processes have a serious drawback in times when the cost of energy increases. Because the recycle desorbent is recovered from both the extract stream and raffinate stream by fractionation, having to fractionate the stream to make a single product makes both light and heavy adsorption processes energy intensive, and, therefore, as energy costs increase, it becomes less and less economical to run either system.

I have now discovered a hybrid process which combines both light and heavy desorbents and in which the adsorption and desorption steps are the same as in the individual light and heavy processes, but which is not as energy intensive as either process. Furthermore, in the hybrid process according to my invention, the need for two fractionating columns for each process is eliminated. Therefore, not only will the energy requirement per pound of product be reduced, but equipment costs for reboiler energy and condensing units used in each process would also be drastically reduced.

It is, therefore, an object of this invention to provide an improved adsorption-desorption process for the separation of closely boiling fractions or isomers of hydrocarbon compounds.

Another object of this invention is to provide an improved adsorption-desorption process which is not energy intensive and which is more cost-efficient than the sum of its individual units.

Another object of this invention is to provide an improved adsorption-desorption process which utilizes an integral light and heavy desorbent process.

Still another object of this invention is to provide an improved adsorption-desorption process for the separation of high purity para-xylene from a xylene feedstream containing mixed xylene isomers.

Other objects and advantages of this invention will become apparent from the detailed description which is to be taken in conjunction with the accompanying drawings in which like numerals indicate like parts and in which.

Although the following detailed description of the figures is directed toward the separation of xylene isomers, other hydrocarbon fractions may be fractionated using like equipment with minor modifications. For example, the same hybrid process may be used for the separations of ethyl benzene and cresols from mixed feedstreams, and low and high octane materials from motor gasoline and diesel fractions.

Figure 1:
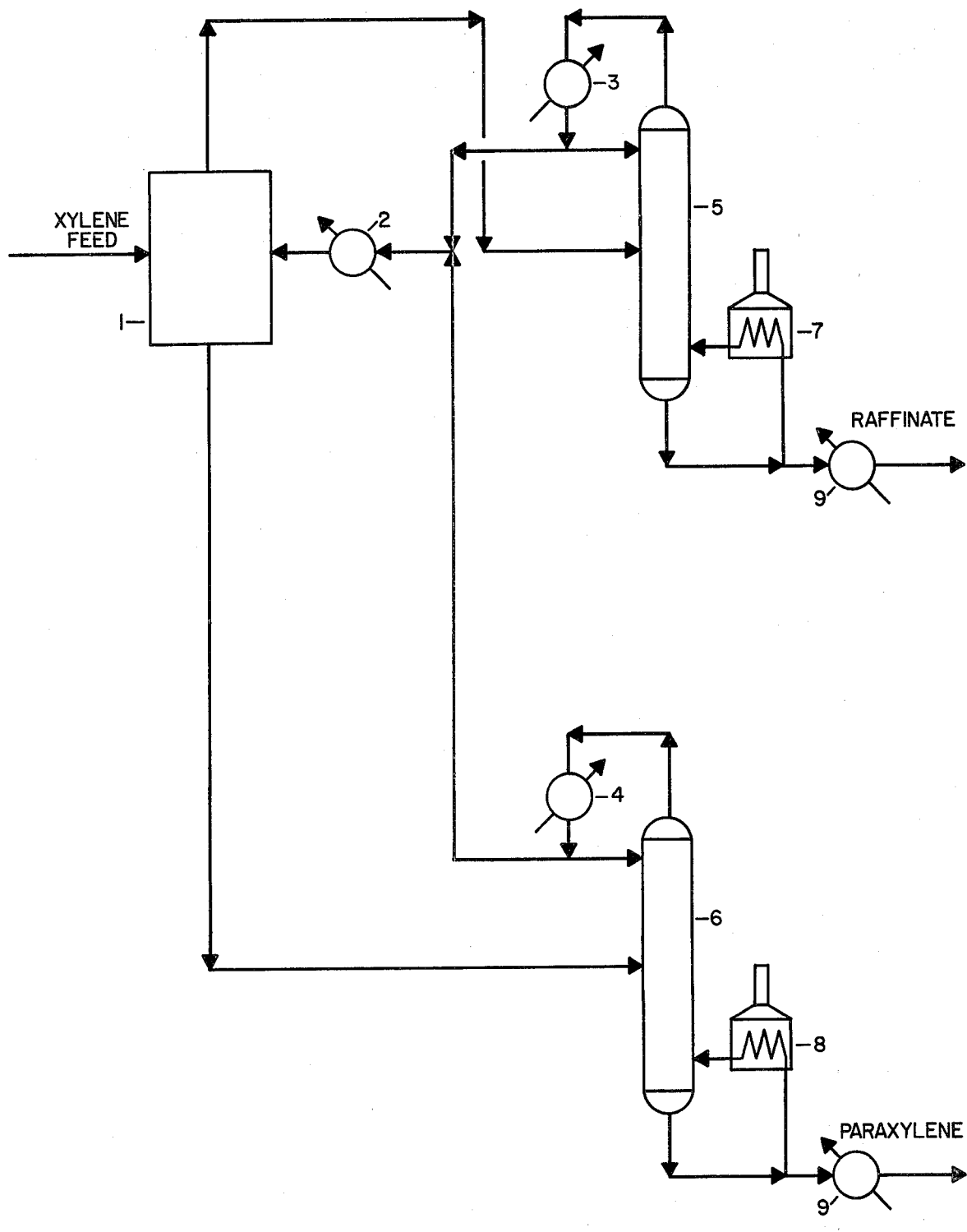
FIG. 1 is a flow schematic of an adsorption-desorption separation process using a light desorbent.

With respect to the light desorbent process of FIG. 1, there is shown a XYLENE FEED (composed of mixed xylene isomers) stream at approximately 315° F., charged into a selective adsorption zone 1 to produce a relatively pure para-xylene extract stream and a relatively para-xylene deficient raffinate stream concentrated in meta- and ortho-xylene, both the extract and raffinate streams being composed of the same diluent (desorbent). Naturally, because each stream is concentrated in different $C_8$ isomers, the extract and raffinate streams have to be kept separate.

The extract stream containing both desorbent and para-xylene is charged into para-xylene fractionation column 6 from which the desorbent (toluene), because it is lighter than the para-xylene feed, comes off overhead through heat exchanger 4 wherein the overhead vapors are condensed, and is either recycled through column 6 or is directed through a heat exchanger 2 to be reintroduced into selective adsorption zone 1.

The now relatively pure, desorbent-free para-xylene, because it is heavier, that is, it boils at a higher temperature than the light desorbent, is taken off the bottom of column 6 and is either heated and recycled through para-xylene reboiler 8 to column 6 or is removed through heat exchanger 9 as para-xylene product.

The raffinate stream, composed of meta- and ortho-xylene in light desorbent is removed from zone 1 and charged into raffinate fractionation column 5 from which the desorbent (toluene), because it is lighter than the mixed isomer feed, comes off overhead through heat exchanger 3 and is either recycled through column 5 or is directed through a heat exchanger 2 to be reintroduced into selective adsorption zone 1.

The now relatively desorbent-deficient raffinate is taken off the bottom of column 5 and is either heated and recycled through raffinate reboiler 7 to column 5 or is removed through heat exchanger 9 as raffinate product.

Figure 2:
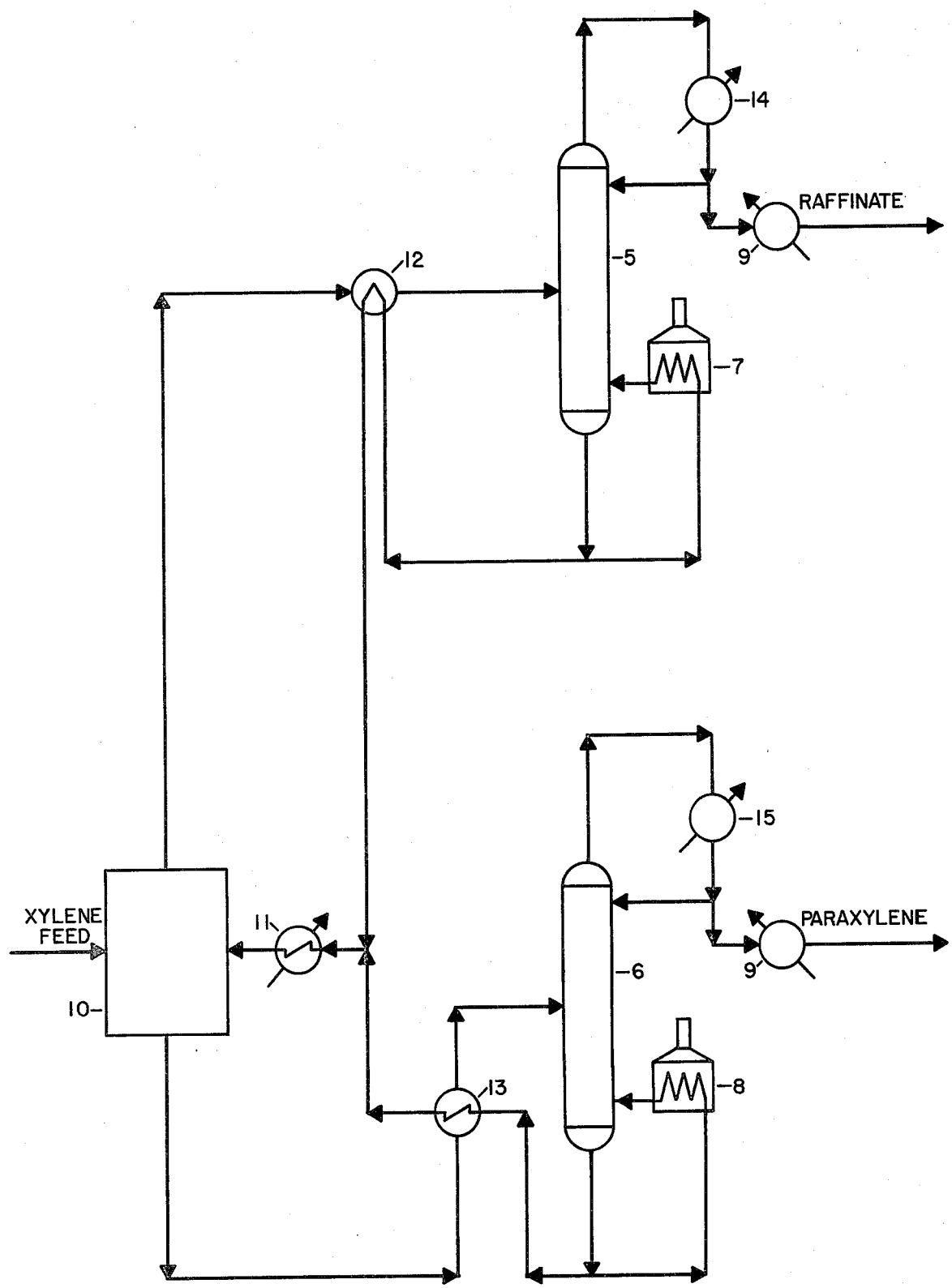
FIG. 2 is a flow schematic of an adsorption-desorption separation process using a heavy desorbent.

A nearly parallel process exists for the heavy desorbent process shown in FIG. 2. The XYLENE FEED stream, at approximately 350° F., is charged into a selective adsorption zone 1 to produce a relatively pure para-xylene extract stream and a relatively para-xylene-deficient raffinate stream. Both streams contain the appropriate xylene isomer concentrated in the heavy desorbent or diluent of the process.

The extract stream containing both heavy desorbent and para-xylene is passed through an indirect heat exchanger 13 to raise its temperature to approximately 415° F. and then is introduced into para-xylene fractionation column 6. The heavy diluent, named because it boils at a temperature higher than para-xylene, comes off the bottom of column 6 and is either heated and recycled through para-xylene reboiler 8 to column 6, or is removed through indirect heat exchanger 13 (thereby releasing heat to the extract stream entering column 6) to pass through a secondary indirect heat exchanger 11 where the stream is cooled and reenters adsorption zone 10.

The now relatively pure, desorbent-free para-xylene, because it is lighter than the heavy desorbent, is taken off the top of the column 6 and is either cooled and recycled through heat exchanger 15 to column 6, or is cooled and removed through heat exchanger 9 as para-xylene product.

The raffinate stream, composed of meta- and ortho-xylene in heavy desorbent is removed from zone 1, heated in an indirect heat exchanger 12, and charged into raffinate column 5 from which the heavy desorbent is removed.

Because the desorbent is heavy, that is, it boils at a temperature higher than the mixed xylene isomers in the raffinate, it is removed from the bottom of the raffinate column and passes either through raffinate reboiler 7, where it is heated, or through indirect heat exchanger 12 (thereby releasing heat to the raffinate stream entering column 5) and through the secondary indirect heat exchanger 11 where the stream is cooled and reenters the adsorption zone 10.

The now para-xylene-free raffinate, because it is lighter than the heavy desorbent, is removed from the top of the column, passed through a heat exchanger 14, where the stream is cooled and either recycled to column 5 or cooled and removed through heat exchanger 9 as raffinate product.

Figure 3:
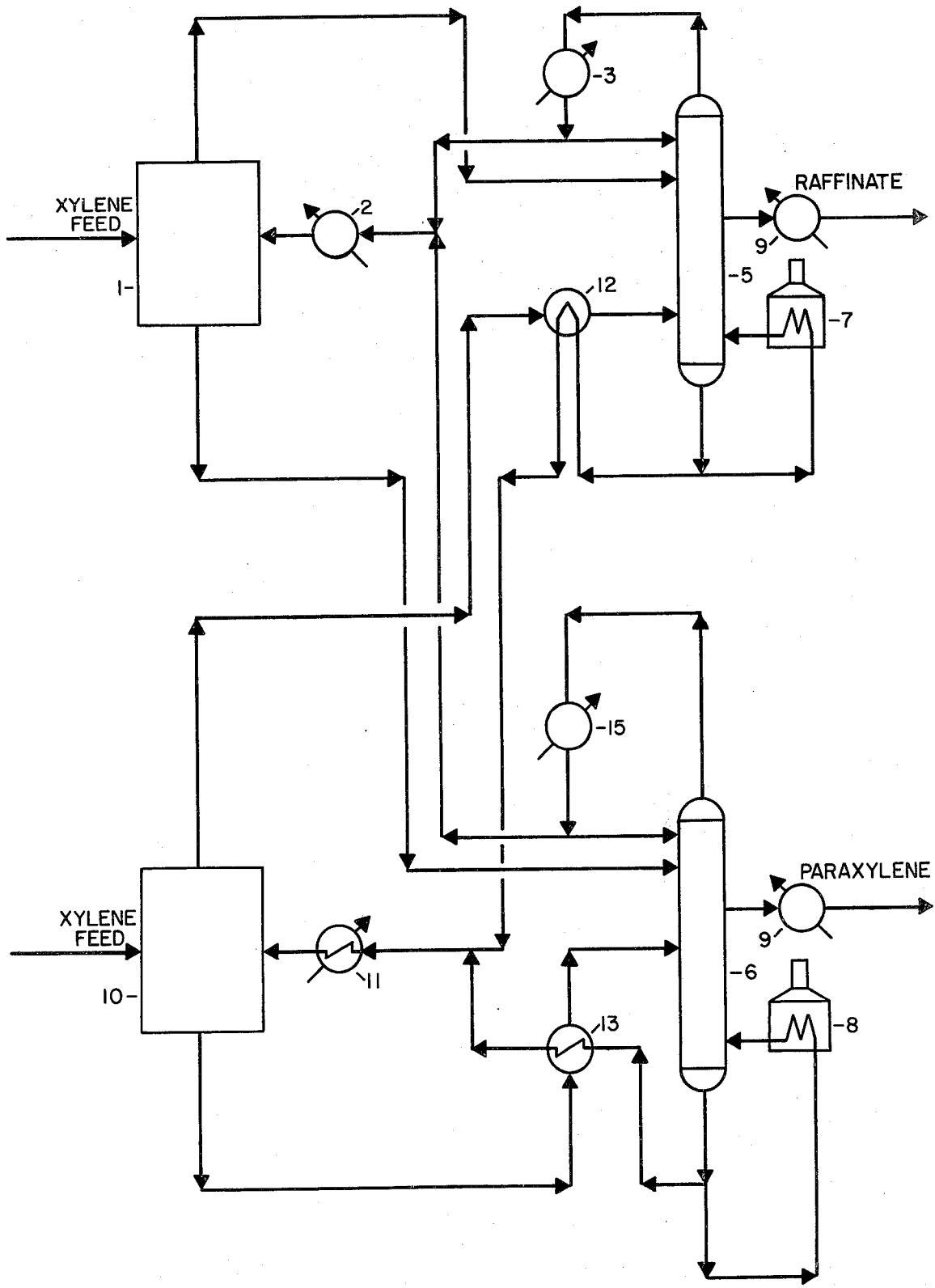
FIG. 3 is a flow schematic of an adsorption-desorption separation process using the integral light and heavy desorbents of the present invention.

In the process according to this invention, and shown in FIG. 3 XYLENE FEED streams composed of mixed xylene isomers are charged separately into a light process adsorption zone 1 (also referred to as light sieve section), and a heavy adsorption zone 10 (also referred to as a heavy sieve section). Adsorption and separation into a raffinate stream and a separate extract stream takes place in both the light and heavy sieve sections as described for FIGS. 1 and 2, above.

The extract and raffinate streams leave their respective adsorption zones and follow the process paths described for FIGS. 1 and 2, above, up to the point that the individual stream enters the raffinate and extract fractionation column. Instead of four separate columns (a light para-xylene column, a light raffinate column, a heavy para-xylene column, and a heavy raffinate column), as would be required in parallel light and heavy process units, the integral process according to this invention requires only a single raffinate column 5, and a single para-xylene column 6.

The light raffinate stream from adsorption zone 1 is passed into raffinate column 5, and the heavy raffinate stream from adsorption zone 10 is passed into raffinate column 5. As described earlier, each raffinate stream will be concentrated with meta- and ortho-xylene in an appropriate light desorbent (such as toluene) and an appropriate heavy desorbent (such as diethyl benzene or durene).

The light extract stream from adsorption zone 1 is passed into para-xylene column 6, and the heavy extract stream from adsorption zone 10 is passed into para-xylene column 6. As in the case of the raffinate stream, each of the two extract streams will contain para-xylene concentrated in a heavy and a light desorbent.

In the fractionation columns, separation of the various stream components is accomplished by the differences of their boiling points. Therefore, as can be seen from the drawing, the light desorbent comes off as a vapor at the top of columns 5 or 6, the raffinate and extract streams are removed as sidestreams, and the heavy desorbent is removed at the bottom of the column.

Specifically, the light extract stream containing both light desorbent and para-xylene is charged into para-xylene fractionation column 6 from which the desorbent, because it is lighter than the para-xylene feed, comes off overhead as vapor and is passed through heat exchanger 15, wherein the vapors are condensed, and is either recycled through column 6 or is directed through heat exchanger 2 to be introduced into sieve section 1. The heavy extract stream containing both heavy desorbent and para-xylene passes through heat exchanger 13 to raise the temperature of the stream and then is charged to para-xylene fractionation column 6, wherein the desorbent, because it is heavier than the para-xylene feed, comes off as liquid bottoms and is either recycled through para-xylene reboiler 8, where it is heated, or through indirect heat exchanger 13 (thereby releasing heat to the extract stream entering column 6) and through the secondary indirect heat exchanger 11 where the stream is cooled and reenters sieve section 10.

The now desorbent-free para-xylene, which would have a boiling range between that of the light and heavy desorbents, is removed from fractionation column 6 as a sidestream and passes through heat exchanger 9, wherein it is cooled and removed as para-xylene product.

The light raffinate stream, composed of meta- and ortho-xylene in light desorbent, is removed from sieve section 1 and charged into raffinate fractionation column 5 from which the desorbent vapor, because it is lighter than the mixed isomer feed, comes off overhead and is cooled in heat exchanger 3 and either recycled through column 5 or is directed through heat exchanger 2 and reintroduced into sieve section 1. The raffinate stream containing xylene isomers in heavy desorbent is removed from sieve section 10, passes through indirect heat exchanger 12, and is charged into raffinate column 5, from which the desorbent, because it is heavier than the mixed isomer feed, is removed as liquid bottoms and is either recycled through raffinate reboiler 7 to column 5 or is directed through indirect heat exchanger 12 (where it releases heat to the raffinate stream being charged to column 5) and is mixed with the heavy desorbent stream from para-xylene column 6, passes through heat exchanger 11, and is reintroduced into sieve section 10.

The now desorbent-free raffinate, which would have a boiling range between that of the light and heavy desorbents, is removed from column 5 as a sidestream and passes through heat exchanger 9 wherein it is cooled and removed as raffinate product.

One specific advantage of this invention, as stated previously and as described above, is that the same reboiler 7 used to boil off the light desorbent from a raffinate is also separating heavy desorbent from the same raffinate as liquid bottoms, and the same reboiler 8 used to boil off light desorbent from an extract stream is also separating heavy desorbent from an extract stream and taking off xylene as sidestreams, whereas in the case of a light adsorption-desorption separation system in parallel with a heavy adsorption-desorption separation system, there would be two additional fractionation columns and two additional reboilers to provide the necessary heat to carry out the separation.

The cost-efficiency of this invention can be seen from the following table which indicates the amount of heat required compared to the amount of product produced:

TABLE

|  | Xylene Feed B/D | Raffinate | Product | Heat $\overline{M}$ Btu/Hr |
|---|---|---|---|---|
| Light Process | 33,700 | 26,800 | 6,900 | 325 |
| Heavy Process | 33,700 | 26,800 | 6,900 | 238 |
| Hybrid Process | 33,700 | 26,800 | 6,900 | 141 |

As shown in the above Table, the amount of heat energy, and therefore the amount of fuel, required by the hybrid process of this invention is 184 $\overline{M}$ Btu/hr. less than required for the light process and 97 $\overline{M}$ Btu/hr. less than required for the heavy process. Furthermore, for a parallel light and heavy process which would also require a total of four fractionation columns, the heat energy required would be approximately 282 $\overline{M}$ Btu/hr. for 6900 B/D of product, a figure which is double that for the hybrid process of this invention.

The hybrid process of this invention, as shown in the above Table, would be able to produce about 2.3 barrels of para-xylene with the same energy required to produce one barrel in the light desorbent process, about 1.6 barrels of para-xylene with the same energy required to produce one barrel in the heavy desorbent process, and about 2.0 barrels of para-xylene with the same energy required to produce one barrel in the parallel heavy-light process. Comparable improved yields would be found with the separation of other hydrocarbon isomers or mixtures.

Thus, while I have illustrated and described the preferred embodiment of my invention, and have described my invention and the manner and process of making and using it in such full, clear, concise and exact terms as to enable any person skilled in the art to which it pertains to make and use the same, one skilled in the art can easily ascertain the essential characteristics of this invention and without departing from the spirit and scope thereof can make various changes and/or modifications to the invention for adapting it to various usages and conditions. Accordingly, such changes and/or modifications are properly intended to be within the full range of equivalents of the following claims.

I claim:

1. In an adsorption-desorption process for separating close boiling materials or isomers in which a liquid desorbent is used to produce an extract of desired materials in said desorbent and also a raffinate of byproduct materials in said desorbent, the improvement which comprises:

carrying out an adsorption-desorption step in a first unit with a desorbent lower boiling than the feedstream to be separated to obtain a light extract and a light raffinate;

carrying out an adsorption-desorption step in a second unit with a desorbent higher boiling than said feedstream to obtain a heavy extract and a heavy raffinate;

passing light raffinate and heavy raffinate into a fractionating column and separating the same by fractionation into light desorbent, heavy desorbent and byproduct raffinate materials;

passing light extract and heavy extract into a second fractionating column and separating the same by fractionation into light desorbent, heavy desorbent and product extracted materials; and recycling light desorbent streams from both fractionators to said first unit and recycling heavy desorbent streams from both fractionators to said second unit.

2. The process of claim 1 wherein the close boiling materials are aromatic compounds.

3. The process of claim 1 wherein the isomers are meta-, ortho-, and para-xylene.

4. The process of claim 1 wherein the lower boiling desorbent is a hydrocarbon compound having seven carbon atoms.

5. The process of claim 1 wherein the higher boiling desorbent is a hydrocarbon containing ten carbon atoms.

* * * * *